United States Patent [19]

Houpis et al.

[11] Patent Number: 5,380,849
[45] Date of Patent: Jan. 10, 1995

[54] PROCESS FOR OPTICALLY PURE DECAHYDROISOQIUNOLINES

[75] Inventors: Ioannis N. Houpis, Edison; Joseph E. Lynch, Plainfield; Audrey Molina, Elizabeth; Ralph P. Volante, Cranbury, all of N.J.

[73] Assignee: Merck & Co., Inc., Rahway, N.J.

[21] Appl. No.: 973,497

[22] Filed: Nov. 9, 1992

[51] Int. Cl.[6] .............................................. C07D 217/00
[52] U.S. Cl. ..................................................... 546/146
[58] Field of Search ......................................... 546/146

[56] References Cited

U.S. PATENT DOCUMENTS 4,381,302  4/1983  Huff ..................................... 514/307
4,902,695  2/1990  Ornstein ............................... 544/344

FOREIGN PATENT DOCUMENTS

432695.A2  6/1991  European Pat. Off. .

OTHER PUBLICATIONS

Kobayashi, S. et al., ". . . Novel Chiral Synthons . . . ," Tetrah. Lett. 25, 2557 (1984).

Levin J. I. et al., ". . . Al–mediated conversion of esters to amides," Synth. Comm. 12, 989 (1982).
Krishnbamarthy, S., ". . . N–Monomethylation of Functionalized Primary Amines . . . ," Tetrah. Lett. 23, 3315 (1982).
Ornstein, P. L. et al., ". . . 6–Oxodecahydroisoquinoline-3-carboxylates . . . ," J. Org. Chem. 56, 4388 (1991).
Lipton M. F. et al.,". . . Dimethylaluminum amides . . . ," Organic Synth., 59, 49 (1978).
Stork, G. et al., "Alkylation and Michael Additions of Glycine Ethyl Ester . . . ," J. Org. Chem. 41, 3491 (1976).
Shiraiwa, T. et al., "Asymmetric Transformation . . . ," Bull. Chem. Soc. 64, 3729 (1991).
Hayashi, K. et al., "Facile Preparation . . . ," Chem. Pharm. Bull. 31, 312 (1983).

Primary Examiner—C. Warren Ivy
Assistant Examiner—Raymond Covington
Attorney, Agent, or Firm—Roy D. Meredith; Jack L. Tribble

[57] ABSTRACT

A process for preparing optically pure decahydroisoquinolines in good yields which avoids difficult purification procedures is described.

4 Claims, No Drawings

PROCESS FOR OPTICALLY PURE DECAHYDROISOQIUNOLINES

BACKGROUND OF THE INVENTION

Decahydroisoquinoline carboxylic acid derivatives, which may be represented by the formula

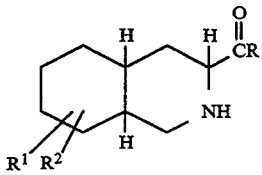

where R is a group which together with the carbonyl forms an acid, acid derivative or ketone, such as OH, NH-alkyl, O-alkyl, S-alkyl, alkyl, aryl, and $R^1$ and $R^2$ independently represent a group or arrangement such as hydroxyl, ketonic oxygen, alkyl or aryl, or when adjacently positioned are arylene or alkylene such as phenylene or 1,4-tetramethylene, are useful as intermediates in the preparation of biologically active compounds. There are many literature references to these compounds. Among the applications is their use in the preparation of N-methyl-D-aspartic acid antagonists as reported by Ornstein, P. L. et al in *J. Org. Chem*, 1991, 56, 4388. The structure shown in a recent publication of a compound potentially useful in the treatment of Acquired Immune Deficiency Syndrome (AIDS), has as part of its structure, N-tert-butyldecahydroisoquinoline-3-carboxamide. Roberts, N. A. et al, *Science* 1990, 248, 358.

A previously reported synthesis for the preparation of N-tert-butyldecahydroisoquinoline-3-carboxamide is that of Hayashi, K. et al., *Chem. Pharm. Bull*, 1983, 31(1), 312, which employed the Pictet-Spengler reaction. This reaction uses L-phenylalanine and formalin in concentrated hydrochloric acid at 95° C. Under these conditions the tetrahydroisoquinoline-3-carboxylic acid derivative obtained had suffered epimerization at the C-3 position. Four steps were required for the resolution of the product so obtained to the required 3-S enantiomer; subsequent hydrogenation of the phenyl ring to the desired decahydroisoquinoline-3-cazboxylic acid produced four possible diastereomers from which the desired diastereomer could only be obtained in a low overall yield. It is desired therefore to find a means for stereospecifically producing decahydroiso-quinoline-3-carboxylic acid and for producing it in a greater yield.

It is a particular object of the present invention to provide a method for producing optically. pure N-tert-butyl-decahydro-4aS,8aS-isoquinoline-3S-carboxamide in good yields.

STATEMENT OF THE INVENTION

According to the present invention, it has been discovered that the desired decahydroisoquinoline compounds represented by the formula

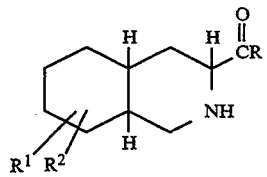

wherein R is OH, O-alkyl, O-aryl, NH-alkyl, S-alkyl, alkyl or aryl and $R^1$ and $R^2$ independently are OH, O, alkyl, aryl or when adjacently positioned are alkylene or arylene may be obtained without loss of optical activity through a sequence of reactions starting from an optically active tetrahydrophthalic mono acid mono

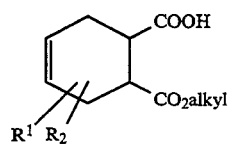

ester. When the product is N-tert-butyldecahydroisoquinoline-3-carboxamide, it may be obtained in an overall yield of at least four times that previously achieved. Furthermore, the starting material, the optically active cis or trans tetrahydrophthalic mono acid mono ester, utilized by this process, may be prepared from commercially available, inexpensive tetrahydrophthalic anhydride rendering the process suitable for large scale production. The desired specific stereochemistry at the ring juncture is readily determined by the appropriate selection of the starting tetrahydrophthalic monoacid mono ester.

DETAILED DESCRIPTION OF THE INVENTION

The novel sequence of reactions in the process of the present invention for producing an optically active decahydroisoquinoline-3-carboxylic acid derivative comprises (1) reacting an optically active tetrahydrophthalic acid, monoalkyl (conveniently monomethyl) ester compound (Compound A) with a carboxylic acid activating agent to obtain a mono-activated acid, monoalkyl ester and thereafter reducing the activated acid/ester intermediate without isolation to obtain the optically active alkyl 2-formylcyclohexane-1-carboxylate (Compound B);

(2) reacting the said alkyl 2-formylcyclohexane-1-carboxylate with a metal enolate of a suitably protected α-amino carbonyl derivative to obtain the condensation product at the aldehyde and thereafter hydrolyzing the condensation product to effect tandem deprotection and cyclization to an optically pure α,β-unsaturated hexahydroisoquinolin-1-one-3-carbonyl derivative (Compound C);

(3) reducing the α,β-unsaturated carbonyl derivative to an optically active alkyl octahydroisoquinolin-1-one-3-carbonyl derivative (Compound D); and (4) reducing said octahydroisoquinoline-1-one-3-carbonyl derivative to obtain the optically active alkyl decahydroisoquinoline-3-carbonyl derivative (Compound I).

The steps may be summarized as follows:

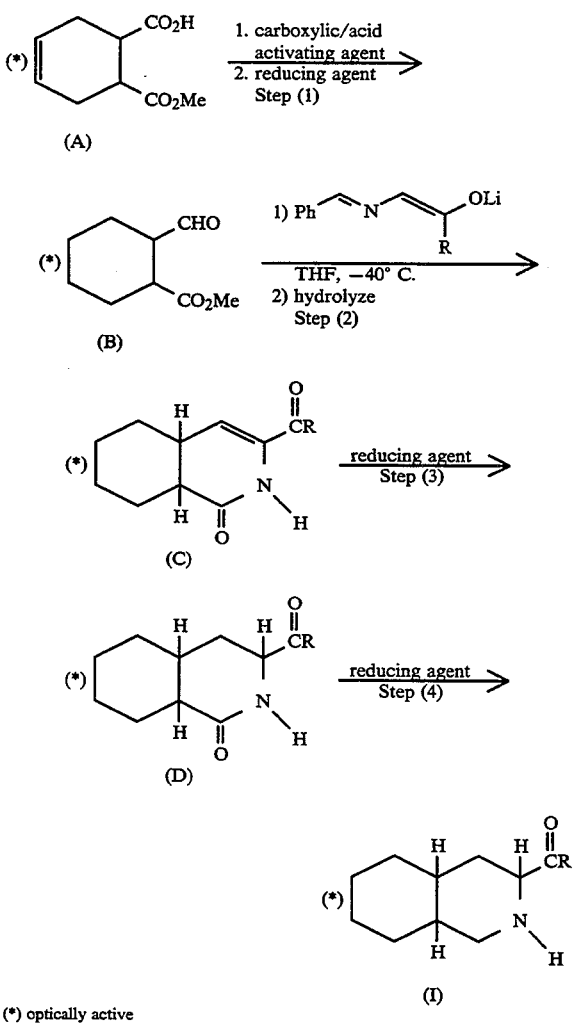

(*) optically active

The foregoing compound designation, e.g. A, B, C, etc. are used to refer to corresponding specific compounds as well as to refer to a generic designation. The reaction step designations also are used whether generic or specific steps are described.

In carrying out Step (1), i.e., the conversion of the monoacid to the aldehyde, the optically active tetrahydrophthalic acid, monoalkyl ester acid (Compound A) is first converted to an activated derivative by adding to a hydrocarbon solution thereof under thoroughly anhydrous conditions under an atmosphere of nitrogen, excess carboxylic acid activating agent also in hydrocarbon solvent. The addition is carried out with stirring at temperatures in the range is −30° to 30° C. for 15 to 25 hours; ambient temperature is preferred. The progress of the reaction is followed by NMR and when the reaction to form the acid derivative is judged to be complete, the solution is concentrated in vacuo and the residue dissolved in THF for the second part of Step (1).

The activated derivative is preferably an acid chloride although it may be an activated ester or anhydride. By "carboxylic acid activating agent" is meant an agent which will form an active acid derivative such as acid chloride, anhydride or certain ester. Oxalyl chloride, thionyl chloride, methyl chloroformate, acyl imidazole, mixed anhydride and the like may be employed to prepare the activated derivative. Oxalyl chloride is preferred, since excess reagent is cleanly removed.

The solvent for the first part of Step (1) is hydrocarbon such as xylene, benzene or preferably toluene.

The second part of Step (1) is reduction. The reduction may be chemical or catalytic. If chemical reduction is to be employed, boron and aluminum hydride such as borohydride, borane, or trihydridoaluminum may be employed. Catalytic reduction is preferred, especially employing palladium on carbon catalyst. In carrying out the reaction, the catalyst and a tertiary-amine, preferably an amine having hindered nitrogen, are added to the THF solution of reactant and the reduction carried out at ambient temperature. About 10 percent by weight of catalyst is generally employed. 2,6-Lutidine is convenient as the amine. The reduction is allowed to take place over a period of about 24 hours. Completion of the reaction is determined by NMR. When the reaction is considered complete, the reduction mixture is separated from the catalyst and solvent, the crude product recovered and dissolved in a solvent such as ethyl acetate or other non water-miscible solvent, and the solution washed sequentially with acid and saturated sodium bicarbonate solution to obtain the optically active alkyl 2-formylcyclohexane-1-carboxylate (Compound B).

Step (2), the conversion of the aldehyde-ester, Compound B, into a hexahydroisoquinolin-1-one-3-carbonyl derivative may be carried out by first forming a metal enolate of suitably protected α-amino carbonyl derivative. By "protected α-aminocarbonyl derivative" is meant that the amino nitrogen of the carbonyl derivative is protected with a conventional amino protecting group and meant to include protection as dibenzyl, disilyl, or amide of carboxylic acid. Preferably this is as the benzaldehyde imine and prepared conveniently in situ, by adding benzylidene α-amino carbonyl derivative to a solution of metal enolate under nitrogen at temperatures in the range −78° to 0° C. throughout the addition. By "metal" in metal enolate is meant any metal capable of forming a soluble enolate such as lithium, potassium, sodium, magnesium, titanium, zirconium and the like. When the protecting group is benzaldehyde imine, the reaction mixture is quenched with methanol/acetic acid and aged for 12 to 24 hours. The hydrolytic aging process appears to be necessary for tandem imine-deprotection and cyclization to obtain the hexahydroisoquinolin-1-one-3-carbonyl compound, (Compound C). After recovery from the reaction mixture by removal of solvent, aging at about −20° C. for 12 to 48 hours produces crystals which may be readily purified by recrystallization or by column chromatography.

Step (3) the reduction of Compound C above prepared, is preferably carried out by hydrogenation using Pd/C catalyst. A pressure of about 40 psi and a temperature of about 35°-40° C. is employed. The product, optically active alkyl octahydroisoquinolin-1-one-3-carboxylate, Compound D, may be recovered in a conventional manner.

Step (4), the conversion of the isoquinolin-1-one carbonyl compound, Compound D, into the desired decahydroisoquinoline-3-carbonyl compound is readily carried out by reduction, preferably a chemical reduction with borane-dimethyl sulfide in anhydrous aprotic solvent at temperatures about 0° C. In carrying out the reaction, borane-dimethyl sulfide is added slowly to a cooled, about 0° C., solution of Compound D, preferably in tetrahydrofuran. It has been found that the optimal temperature for the addition of borane is about 0° C. When the carbonyl compound is an ester, higher temperatures oftentimes lead to overreduction to an alcohol at the 3-position, i.e., the group at this position becomes hydroxymethyl instead of remaining methoxycarbonyl. After concluding the addition, the reaction mixture is aged to complete the reduction.

The reaction is then quenched with methanol at 0° C., and the mixture concentrated in vacuo to obtain Compound (I), optically active decahydroisoquinoline-3-carbonyl compound as the amine-borane complex or if ester, then alkyl decahydroisoquinoline-3-carboxylate as the complex. Compound (I) may be separated from the complex by adding a borane-decomplexing agent to the complex. By "borane-decomplexing agent" is meant any number of reagents including $F^-$, alkylamines, aminoalcohols, aqueous acid and the like which are customarily employed for decomplexing. In a preferred procedure, a large excess (5 equivalents) of n-propylamine in toluene at 45° C., is added to decomplex and Compound (I) recovered from the mixture by (a) partitioning between hexane or other hydrocarbon and dilute HCl at about 0° C., (b) basifying the aqueous layer to pH 10 and (c) extracting with a water-immiscible solvent. Ethyl acetate or other aprotic solvent may be employed. It is critical and essential that dilute acid be used and the temperature be maintained at about 0° C. during the work up since the product is quite labile under strongly acidic conditions at ambient temperature. The use of $BH_3.THF$ as the reducing agent as well as the addition of $BH_3.SMe_2$ at temperatures >25° C. produces substantial amounts of product in which the ester group is reduced to a hydroxymethyl group.

The starting material for the foregoing sequence of steps, optically active tetrahydrophthalic acid monomethyl ester (A), while not available commercially may be easily prepared from readily commercially available meso-cis-tetrahydrophthalic anhydride (X) in a number of ways including a two step chemical procedure of (1) basic hydrolysis followed by (2) reacting with an optically active base and recrystallyizing to obtain the optically active mono acid; or an alternative procedure of enzymatic hydrolysis with pig liver esterase using a procedure described by Kobayashi, et al *Tetrahedron Lett.* 1984, 25,2557, whereby the desired mono ester starting material (A) may be obtained directly from the commercially available (X).

When the particular optically pure decahydroisoquinoline product desired is N-tert-butyldecahydro-4a,8a-isoquinoline-3-carboxamide, then Compound (I) prepared as an ester may be reacted with an alkyl aluminum amine reagent to form an amide complex which may then be hydrolyzed to the desired carboxamide (Compound IA). This is an alternative procedure to using an amide as the α-aminocarbonyl derivative in Step (2). The alkyl aluminum amine reagent is first prepared by mixing together a trialkyl aluminum solution in anhydrous aprotic solvent, preferably toluene-tetrahydrofuran with neat tertiary butylamine at ambient temperatures, then warming to about 45° C. and maintaining at that temperature for about 30 minutes to complete the formation of the reagent. Other aprotic solvents may be employed but THF or combinations thereof are preferred. The reaction is exothermic and, external cooling to about 0° C. is necessary. After completion of the addition, the mixture is warmed to 40°–45° C. for about 0.5 to 1 hour then cooled to 23° C. and the aprotic solvent solution of the alkylamine reagent is added at this temperature to an aprotic solvent solution of Compound I, as the 3-carboxylate ester prepared as above-described and the mixture stirred for 60–70 hours at ambient temperature. The relative amounts of the reactants are about three moles of the reagent for each mole of the ester being converted. After 45 to 55 hours, additional reagent is added to insure completion of the reaction. Completion of the reaction may be determined by TLC preferably using 5:1 ethyl acetate/hexane with ninhydrin stain. When completion of the reaction has been established, the mixture is transferred to a saturated solution of potassium, sodium tartrate, then ethyl acetate is added and the resulting biphasic mixture vigorously stirred until both layers are clear. This may take several hours. The pH of the aqueous layer is then adjusted to about 11, the organic layer is dried over $MgSO_4$ and then concentrated in vacuo. The residue may be purified by chromatography on silica gel which has been deactivated with 2 percent triethylamine in hexane and using 1:1 ethyl acetate:hexane as eluent.

When some other amide is desired, the appropriate amine is substituted for the tertiary butyl amine.

A preferred application of this process is the preparation of an optically active decahydroisoquinoline-3-carboxylic acid ester. This preparation is carried out by (1) adding to a dry solution of optically active tetrahydrophthalic acid mohoalkyl ester in hydrocarbon solvent at a temperature in the range of −30° to 30° C. under an atmosphere of nitrogen, a hydrocarbon solution of a carboxylic acid activating agent to obtain an activated tetrahydrophthalic ester, replacing the solvent to an ethereal solvent and hydrogenating the solution over Pd/C in tertiary-amine to obtain optically active alkyl 2-formylcyclohexane-1-carboxylate (aldehyde ester; Compound B);

(2) adding a solution of the aldehyde ester in an aprotic solvent and cooled to below 0° C., a metal enolate of benzylidene glycine methyl ester prepared in situ by adding benzylidene methyl ester to a solution of metal bis(trimethylsilyl)amide under nitrogen at temperatures between −78° to 0° C., thereafter quenching with methanol/acetic acid and aging for 12 to 24 hours, then by removing alkali soluble material and chromatographing recovering as the product, optically active alkyl hexahydroisoquinolin-1-one-3-carboxylate (Compound C);

(3) hydrogenating the optically active ester on Pd/C catalyst at 40 psi and temperatures of 35°–40° C. and recovering, optically active alkyl octahydroisoquinolin-1-one-3-carboxylate (Compound D) in a conventional manner, and (4) adding borane-dimethyl sulfide to a cooled to 0° C. solution of Compound D in tetrahydrofuran while maintaining the temperature below 0° C., then allowing the reaction mixture to warm to room temperature to complete the reaction; thereafter cooling to 0° C., adding methanol and decomplexing agent to quench the reaction, and warming to about 45° C., to complete the decomplexing and then recovering Compound I by conventional procedures.

A process for preparing optically active N-tert-butyl-decahydroisoquinoline-3-carboxamide (Compound IA) comprises the additional step of (5)(a) adding a solution of optically active alkyl decahydroisoquinoline-3-carboxylate prepared. according to Step 4 to a dry tetrahydrofuran solution of an aluminum amine reagent prepared by intimately mixing a 1M solution of trialkylaluminum in toluene with t-butylamine in 1:1 tetrahydrofuran:toluene at 45° C. for about thirty minutes, concentrating and recovering as residue and (b) dissolving the residuein dry tetrahydrofuran, aging at ambient temperature for 24 hours and then quenching, preferably with Na, K tartate.

The foregoing process as applied to the preparation of a specific compound, N-tert-butyldecahydro-4aS,-8aS-isoquinoline-3S-carboxamide, Compound IA, may be seen in the following flow diagram which includes the steps of preparing the starting material from a commercially available meso anhydride and also the final step of preparation N-butylamide. (The prime (') after the letters of the compound in the flow diagram is for the specific stereospecific compound within the generic designation employed heretofore.)

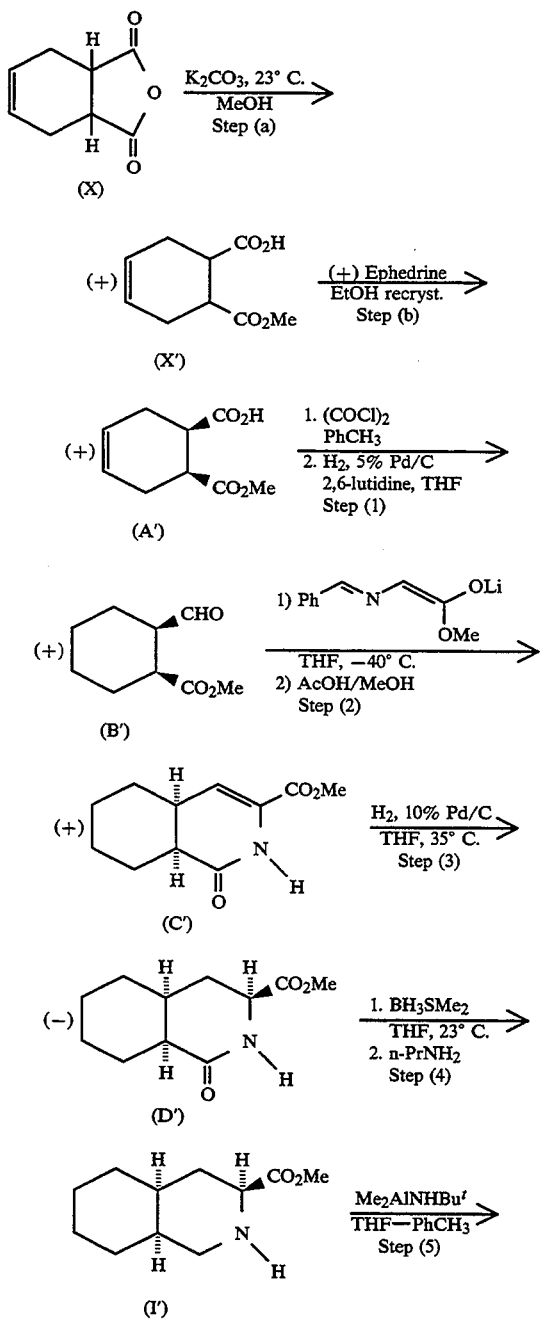

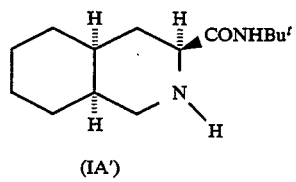

The sequence of steps constituting the present invention as applied specifically to the preparation of an alkyl decahydro (4aS,8aS) isoquinoline-3S-carboxylate and to the preparation of N-tert-butyl-decahydro-4aS, 8aS-isoquinoline-3S-carboxamide from Compound A' in the flow diagram comprises:

(1) intimately mixing together (1S,2R)-tetrahydrophthalic acid monoalkyl ester and oxalyl chloride in toluene at ambient temperature with a continuous nitrogen purge to obtain a mono-acid chloride monoalkyl ester, hydrogenating said acid chloride on Pd/C catalyst in the presence of hindered nitrogen base to obtain the aldehyde ester, alkyl 2-formyl(1S,2R)cyclohexane-1-carboxylate, (2)(a) adding the aldehyde ester to a solution in tetrahydrofuran of an enolate of benzylidene glycine methyl ester at −40° C., said benzylidene glycine methyl ester prepared in situ by reacting benzylidine glycine methyl ester with lithium hexamethyldisilylazide, and thereafter adding acetic acid in anhydrous methanol to quench the reaction, and recovering a crude product of condensation between the aldehyde and the glycine at the alpha carbon as residue, and (2)(b) adding to the residue a large excess of acetic acid in anhydrous methanol for 30–40 hours at 20°–25° C. to effect tandem imine deprotection and cyclization to obtain a cyclic amide, alkyl hexahydro-4aS,8aS-isoquinolin-1-one-3-carboxylate;

(3) hydrogenating the cyclic amide thus obtained over Pd/C to obtain alkyl octahydro-(4aS,8aS) isoquinolin-1-one-3S-carboxylate, and (4)(a) reducing the alkyl octahydro(4aS,8aS)-isoquinolin-1-one-3S-carboxylate thus obtained by adding excess neat borane-dimethyl sulfide to a THF solution thereof at 0° C. followed by aging to obtain in the reaction mixture the alkyl decahydro(4aS,8aS)-isoquinoline-3S-carboxylate product complexed with the borane and (4)(b) treating the complex with decomplexing agent to obtain an alkyl decahydro(4aS,8aS)isoquinoline-3S-carboxylate product; and (5)(a) adding a solution of alkyl decahydro (4aS,8aS-)isoquinoline-3S-carboxylate to a dry tetrahydrofuran solution of an aluminum amine reagent prepared by intimately mixing a 1M solution of trialkyl aluminum in toluene with t-butylamine in 1:1 tetrahydrofuran:toluene at 45° C. for about thirty minutes, concentrating and recovering as residue and (5)(b) dissolving the residue in dry tetrahydrofuran, aging at 23° C. for 24 hours and thereafter quenching with Na, K tartrate to obtain N-tert-butyl-decahydro-4aS,8aS-isoquinoline-3S-carboxamide.

Preparation of Starting Material

The starting material in the foregoing sequence of reactions, monoalkyl tetrahydrophthalate, Compound A, may be obtained from tetrahydrophthalic anhydride, Compound X, first by hydrolysis in alkanol at ambient temperature according to Step (a) of the flow diagram to obtain tetrahydrophthalic acid monoalkyl ester, Compound X'. The mono acid may be resolved by reacting with (+) ephedrine or other optically active base to obtain the diastereomeric salts of (+) ephedrine (or other base). The optical purity of the salt may be upgraded by about two recrystallizations. The salt may then be dissolved in acid and the mixture extracted with diethyl ether. The diethyl ether solution after washing and drying may be concentrated to obtain the optically pure acid starting material (A).

It is noted that there are numerous ways to obtain this starting material. One other way may be by the treatment of the tetrahydrophthalic anhydride with thionyl chloride and methanol. An enzymatic method with pig liver esterase on the dimethylester has previously been noted.

The following examples illustrate the invention but are not to be construed as limiting:

Example 1

A. Monomethyl racemic tetrahydrophthalate (Compound X')

421.5 grams (3.05 mole) of potassium carbonate was slowly added as a solid to a solution of 185.76 grams (1.22 mole) of meso tetrahydrophthalic anhydride at a rate such that the temperature did not rise above 31° C. The reaction was followed with NMR and when it was determined to be complete, concentrated HCl was added slowly and carefully and continued until pH of 1 was reached. The mixture was then extracted with ethyl acetate. The organic extract was dried over MgSO$_4$, filtered and concentrated in vacuo to produce 179.7 grams (80%) of the racemic monomethyl phthalate (monoacid).

B. Optically Pure (+) Monomethyl Tetrahydrophthalate (Monoacid) (Compound A)

To a solution of 121.3 grams (0.696 mole) of (+) ephedrine in 950 milliliters of ethanol at 70° C. was added slowly via addition funnel 128.23 grams <0.696 mole) of (±)-monomethyl tetrahydrophthalate in 800 milliliters of ethanol. When the addition was complete, the funnel was rinsed with an additional 150 milliliters of ethanol and mixture allowed to cool gradually. When the mixture reached about 25° C., the salt started to precipitate and the resulting slurry was allowed to age overnight with agitation. The mixture was cooled to 0° C. for two hours and then filtered. The filter cake was washed with 200 milliliters of ethanol (at 0° C.) and dried in vacuo to obtain 93.94 grams of the ephedrine salt (38% yield; enantiomeric excess (ee)).

The optical purity of the salt was upgraded by two recrystallizations from ethanol to obtain salt in about 30 percent yield and 99 percent ee. The salt was then dissolved in 150 milliliters of 2N H$_2$SO$_4$ and extracted with 300 milliliters of diethyl ether. The organic solution was washed with 200 milliliters of 2N sulfuric acid and 200 milliliters of water and dried over MgSO$_4$ and the dried solution concentrated in vacuo to obtain 37.18 grams of the optically pure acid (29% yield).

C. Methyl 2-formyl(1S,2R)cyclohexane-1-carboxylate (Compound B)

To a solution of 39.4 grams (214 mmol) of the "mono acid" prepared above and azeotropically dried in 1.1 liters of toluene, was added and intimately mixed, 22.4 milliliters (257 mmol) of oxalyl chloride at 23° C. The reaction was not observably exothermic during the addition; after completion of the addition, the reaction mixture was stirred at 23° C. for 18 hours. A stream of nitrogen was passed through the solution to remove the HCl produced. When the reaction was judged complete by NMR, the mixture was subjected to reduced pressure to remove some of the toluene to obtain a residue of the acid chloride. The latter was dissolved in 1.1 liter of THF and transferred to a Parr vessel and to it was added 25.4 ml of 2,6-lutidine and 3.9 grams of Pd/C and the mixture hydrogenated at 40 psi at 25° C. for 24 hours. On completion of the reaction as determined by NMR, the mixture was filtered, the filter cake washed with ethyl acetate, the filtrate concentrated in vacuo. The residue was redissolved in ethyl acetate and washed sequentially with 1N HCl and saturated aqueous sodium bicarbonate. The ethyl acetate solution was dried and concentrated in vacuo to obtain 32.0 grams of the aldehyde, Compound B (a yield of 88 percent from the monoacid, Compound A). The compound had optical rotation $[\alpha]^{23} = +40.3°$ (c=1, CH$_3$OH).

D. Methyl hexahydro-4aS, 8aS-isoquinolin-1-one-3-carboxylate (Compound C)

A solution of 33.82 grams (190.0 mmole) of amine protected glycine methyl ester in 145 milliliters of tetrahydrofuran was added to a solution of lithium bis(trimethylsilyl)amide in 435 milliliters of THF at −40° C. under nitrogen atmosphere while the temperature was maintained between −40° and −35° C. The resulting solution was aged for 30 minutes to obtain the reagent, C$_6$H$_5$—CH=N—CH=C(OLi)(OCH$_3$).

To the solution of the reagent, thus prepared, was added a solution of 31.0 grams (182.35 mmole of the aldehyde prepared in Part C in 65 milliliters of THF over a period of 15 minutes while the temperature was maintained at −40° C. After additional 30 minutes at −40° C. when the starting was found to have been consumed [as determined by TLC (9:1 hexane:ethyl acetate) and NMR], the reaction was quenched with a solution of 60 milliliters of acetic acid and the volatiles were then evaporated in vacuo. The crude residue examined by NMR which showed the presence of two diastereomers of intermediate lactone (Rf=0.41 and 0.35; 3:1 hexane-ethyl acetate) and a trace of the desired methyl hexahydro(4aS,8aS)isoquinolin-1-one-3-carboxylate (Rf=0.3; 3:1 hexane-ethyl acetate). 350 milliliters of methanol and 50 milliliters of acetic acid were then added to the residue and the mixture aged for 17 hours at ambient temperature.

The mixture was concentrated in vacuo, the residue diluted with ethyl acetate and 5N aqueous NaOH added until the pH was greater than 11. The organic layer was dried over MgSO$_4$ and concentrated in vacuo. The residue was chromatographed (3:1 hexane:acetic acid) through a short flash column and two fractions were obtained: the first, amounting to 22.6 grams contained about 10 percent of the lactone while the second, amounting to 9.64 grams contained pure product (Compound C). The first fraction was subjected again to hydrolysis (200 mL CH$_3$OH, 40 mL acetic acid), and after repeating the work-up, aged at −20° C. for seven days to obtain crystals of Compound C which were slurried with hexane to obtain 12.26 grams of C and the mother liquors chromatographed to obtain additional 6.1 grams. The total yield of Compound C was 28.1 grams (73 percent from Compound B). $[\alpha]^{24} = +58.0°$ (C=1, CH$_3$OH).

E. Preparation of Methyl Octahydro(4aS,8aS-)isoquinolin-1-one-3S-carboxylate (Compound D)

A solution of 27.6 grams (131.4 mmole) of Compound C in 280 milliliters of THF in a hydrogenation vessel was charged with 2.7 grams of 10% Pd/C and the mixture hydrogenated at 40 psi at 35° C. for 24 hours. As soon as the reaction was judged complete by NMR, the mixture was filtered, the filtrate concentrated in vacuo, the residue dissolved in ethyl acetate, filtered through a pad of MgSO$_4$, and the filtrate concentrated to obtain Compound D in essentially quantitative yield (28 grams). $[\alpha]^{23}=9.2°$ (C=1, CH$_3$OH).

F. Methyl Decahydro(4aS,8aS)isoquinoline-3S-carboxylate (Compound I)

The isoquinolinone prepared above was dissolved in 50 milliliter of tetrahydrofuran and cooled to 0° C. The borane-dimethylsulfide complex (2.81 mL) was added neat in a manner that the temperature did not exceed 0° C. The solution was warmed to ambient temperature for 2 hours when it was judged complete by NMR analysis. The mixture was recooled to 0° C., quenched with methanol and concentrated in vacuo. The residue was dissolved in 50 milliliters of toluene and 6 milliliters of n-propyl amine were added and the mixture heated to 45° C. After about one hour, the crude NMR showed that the product was completely decomplexed from the borane. The solvent was concentrated in vacuo and the residue partitioned between 0.25M aqueous HCl (150 mL) and 50 mL hexane at −10° to 0° C. 1N NaOH was added to the aqueous layer and stirred at 0° C. until pH=10. Then ethyl acetate was added and the organic layer dried with MgSO$_4$ and concentrated in vacuo to yield the pure product in 77% yield (1.92 gr).

G. Preparation of Compound IA 3.6 milliliters of 0.5M solution of triisobutyl aluminum in toluene was mixed at 0° C. with 0.38 milliliter of tert-butylamine. The mixture was warmed first to ambient temperature and then to 45° to 50° C. and maintained there for about 30 minutes. The solvent was removed in vacuo at 45° C. and the residue cooled to ambient temperature, and to it was added methyl decahydro(4aS,8aS)isoquinoline-3S-carboxylate Step F in 4 milliliters of tetrahydrofuran. The mixture was stirred for 48 hours at ambient temperature. When the reaction was judged complete by TLC (5:1 ethyl acetate:hexane; ninhydrin stain) the mixture was transferred to a saturated solution of K, Na tartrate. Ethyl acetate was added and the biphasic mixture vigorously stirred until both layers were clear (1–2 hours). The pH of the aqueous layer was adjusted to about 11, the layer separated, the organic layer dried over MgSO$_4$ and concentrated in vacuo. Chromatography on SiO$_2$ deactivated with 2 percent triethylamine in hexane and 1:1 ethyl acetate-hexane as eluent yielded 186 mg of product, Compound IA in a yield of 65 percent (with the ratio of desired $\beta$ C-3 epimer to undesired $\alpha$ isomer=95:5) $[\alpha]^{28}=69.5°$ (c=0.52, CH$_3$OH)

Preparation of Other Derivatives

When other derivatives are desired, the methyl or alkyl decahydro(4aS,8aS)isoquinoline-3S-carboxylate (Compound I) may be reacted in a manner known to the skilled in the art to convert the ester group to an acid, acid derivative or ketone group without affecting the stereospecificity.

What is claimed is:

1. A process for producing optically active decahydroisoquinoline-3-carboxylic acid ester comprising
    (1) adding to a dry solution of optically active tetrahydrophthalic acid monoalkyl ester (Compound A) in hydrocarbon solvent at a temperature in the range of −30° to 30° C. under an atmosphere of nitrogen, a hydrocarbon solution of a carboxylic acid activating agent to obtain an activated tetrahydrophthalic ester, replacing the solvent to an ethereal solvent and hydrogenating the solution over Pd/C in tertiary-amine to obtain optically active alkyl 2-formylcyclohexane-1-carboxylate (aldehyde ester; Compound B);
    (2) adding a solution of the aldehyde ester in an aprotic solvent and cooled to below 0° C., a metal enolate of benzylidene glycine methyl ester prepared in situ by adding benzylidene methyl ester to a solution of metal bis(trimethylsilyl)amide under nitrogen at temperatures between −78° to 0° C., thereafter quenching with methanol/acetic acid and aging for 12 to 24 hours then recovering the product, optically active alkyl hexahydroisoquinolin-1-one-3-carboxylate (Compound C) by removing alkali soluble material and chromatographing;
    (3) hydrogenating the optically active ester on Pd/C catalyst at 40 psi and temperatures of 35°–40° C. and recovering, optically active alkyl octahydroisoquinolin-1-one-3-carboxylate (Compound D) in a conventional manner;
    (4) adding borane-dimethyl sulfide to a cooled to 0° C. solution of alkyl octahydroisoquinolin-1-one-3-carboxylate (Compound D) in tetrahydrofuran while the temperature is maintained below 0° C., then allowing the reaction mixture to warm to room temperature to complete the reaction; thereafter cooling to 0° C., and adding methanol and decomplexing agent to quench the reaction, and warming to about 45° C., to complete the decomplexing and thereafter recovering Compound I by conventional procedures.

2. A process for producing an optically active N-tert-butyl-decahydroisoquinolin-3-carboxamide comprising adding a solution of optically active alkyl decahydroisoquinoline-3-carboxylate prepared according to claim 1 to a dry tetrahydrofuran solution of an aluminum amine reagent prepared by intimately mixing a 1M solution of trialkylaluminum in toluene with t-butylamine in 1:1 tetrahydrofuran:toluene at 45° C. for about thirty minutes, concentrating and recovering as residue, and dissolving the residue in dry tetrahydrofuran and aging at ambient temperature for 24 hours and thereafter quenching preferably With Na,K tartate.

3. A process for producing a decahydro-4aS, 8aS-isoquinoline-3S-carboxylic acid ester comprising
    (1) intimately mixing together (1S,2R)tetrahydrophthalic acid monoalkyl ester and oxalyl chloride in toluene at ambient temperature with a continuous nitrogen purge to obtain a mono-acid chloride monoalkyl ester, hydrogenating said acid chloride on Pd/C catalyst in the presence of hindered nitrogen base to obtain the aldehyde ester, alkyl 2-formyl(1S,2R)cyclohexane-1-carboxylate,
    (2)(a) adding the aldehyde ester to a solution in tetrahydrofuran of an enolate of benzylidene glycine methyl ester at −40° C., said benzylidene glycine methyl ester prepared in situ by reacting benzylidine glycine methyl ester with lithium hexamethyldisilylazide, and thereafter adding acetic acid in anhydrous methanol to quench the reaction, and recovering a crude product of condensation between the aldehyde and the glycine at the alpha carbon as residue, and (b) adding to the residue a large excess of acetic acid in anhydrous methanol for 30–40 hours at 20°–25° C. to effect tandem imine deprotection and cyclization to obtain a cyclic amide, alkyl hexahydro-4aS,-8aS-isoquinolin-1-one-3-carboxylate, (3) hydrogenating the cyclic amide thus obtained over Pd/C to obtain alkyl octahydro-(4aS,8aS) isoquinolin-1-one-3S-carborylate, and (4)(a) reducing the alkyl octahydro(4aS,8aS)-isoquinolin-1-one-3S-carboxylate thus obtained by adding excess neat borane-dimethyl sulfide to a THF solution thereof at 0° C. followed by aging to obtain in the reaction mixture the alkyl decahydro(4aS,8aS)-isoquinoline-3S-carboxylate product complexed with the borane, and (b) treating the complex with decomplexing agent to obtain an alkyl decahydro(4aS,8aS)isoquino-line-3S-carboxylate product.

4. A process for preparing N-tert-butyldecahydro-4aS,8aS-isoquinoline-3S-carboxamide which comprises the additional step of (a) adding a solution of alkyl decahydro<4aS,8aS)isoquinoline-3S-carboxylate prepared according to claim 3 to a dry tetrahydrofuran solution of an aluminum amine reagent prepared by intimately mixing a 1M solution of trialkyl aluminum in toluene with t-butylamine in 1:1 tetrahydrofuran:toluene at 45° C. for about thirty minutes, concentrating and recovering as residue and (b) dissolving the residue in dry tetrahydrofuran, and dissolving the residue in dry tetrahydrofuran and aging at 23° C. for 24 hours and thereafter quenching with Na, K tartrate.

* * * * *